(12) United States Patent
Beale et al.

(10) Patent No.: US 11,497,573 B2
(45) Date of Patent: *Nov. 15, 2022

(54) SURGICAL DRAPING SYSTEM AND METHOD FOR USING SAME

(71) Applicant: Warsaw Orthopedic, Inc., Warsaw, IN (US)

(72) Inventors: Jeffrey W. Beale, Bartlett, TN (US); Robert Andrew Fields, Memphis, TN (US); Richard Hynes, Melbourne Beach, FL (US); Matthew Morrison, Cordova, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 238 days.

This patent is subject to a terminal disclaimer.

(21) Appl. No.: 16/902,679

(22) Filed: Jun. 16, 2020

(65) Prior Publication Data

US 2020/0305995 A1 Oct. 1, 2020

Related U.S. Application Data

(63) Continuation of application No. 15/405,090, filed on Jan. 12, 2017, now Pat. No. 10,729,507.

(51) Int. Cl.
*A61B 46/20* (2016.01)
*A61B 46/00* (2016.01)
*A61G 13/12* (2006.01)

(52) U.S. Cl.
CPC .............. *A61B 46/20* (2016.02); *A61B 46/00* (2016.02); *A61B 46/40* (2016.02); *A61B 2046/205* (2016.02); *A61G 13/122* (2013.01)

(58) Field of Classification Search
CPC ......... A61B 46/27; A61B 46/30; A61B 46/00; A61B 2046/236; A61B 46/10;
(Continued)

(56) References Cited

U.S. PATENT DOCUMENTS

| 4,730,609 A | 3/1988 | McConnell |
| 5,713,372 A | 2/1998 | Pinney et al. |

(Continued)

FOREIGN PATENT DOCUMENTS

| CN | 102397105 | 4/2012 |
| CN | 205215357 | 5/2016 |

(Continued)

OTHER PUBLICATIONS

US 6,216,701 B1, 04/2001, Heaton et al. (withdrawn)

(Continued)

*Primary Examiner* — Caitlin A Carreiro

(57) ABSTRACT

A surgical draping system includes an under-draping, an over-draping, and a connecting draping connected between the under-draping and the over-draping. The surgical draping system is used to establish and maintain a surgical corridor to a surgical site or sites on a patient supported by a surgical table. The surgical draping system can accommodate rotation of the patient on the surgical table, such that the sterile surgical corridor is maintained even during such rotation. The sterile surgical corridor extends through an aperture formed in the over-draping, through an enclosed passageway formed through the connecting draping, and through an aperture formed in the under-draping.

19 Claims, 14 Drawing Sheets

(58) Field of Classification Search
CPC ... A61B 46/20; A61B 46/40; A61B 2046/205; A61G 13/04; A61G 13/122
USPC .......... 128/849, 850, 853, 854, 898; 5/607
See application file for complete search history.

(56) References Cited

U.S. PATENT DOCUMENTS

| | | | |
|---|---|---|---|
| 5,778,891 A | 7/1998 | McMahan | |
| 5,803,086 A | 9/1998 | Scholz et al. | |
| 5,832,925 A | 11/1998 | Rothrum | |
| 5,845,641 A | 12/1998 | Pinney et al. | |
| 5,857,467 A | 1/1999 | Faries, Jr. et al. | |
| 5,871,014 A | 2/1999 | Clay et al. | |
| 5,891,812 A | 4/1999 | Honeycutt et al. | |
| 5,901,706 A | 5/1999 | Griesbach et al. | |
| 5,921,242 A | 7/1999 | Newman | |
| 5,975,082 A | 11/1999 | Dowdy | |
| 5,979,450 A | 11/1999 | Baker et al. | |
| 5,985,395 A | 11/1999 | Comstock et al. | |
| 6,032,670 A | 3/2000 | Miller | |
| 6,037,281 A | 3/2000 | Mathis et al. | |
| 6,105,579 A | 8/2000 | Levitt et al. | |
| 6,138,676 A | 10/2000 | Bruhn | |
| 6,167,885 B1 | 1/2001 | Hanssen | |
| 6,237,600 B1 | 5/2001 | Simard | |
| 6,286,511 B1 | 9/2001 | Levitt et al. | |
| 6,298,855 B1 | 10/2001 | Baird | |
| 6,302,109 B1 | 10/2001 | Parnes | |
| 6,345,621 B1 | 2/2002 | Chandler et al. | |
| 6,345,622 B1 | 2/2002 | Chandler et al. | |
| 6,345,623 B1 | 2/2002 | Heaton et al. | |
| 6,357,445 B1 | 3/2002 | Shaw | |
| 6,367,104 B1 | 4/2002 | Fallbo, Sr. et al. | |
| 6,394,095 B1 | 5/2002 | Idman et al. | |
| 6,405,730 B2 | 6/2002 | Levitt et al. | |
| 6,520,184 B2 | 2/2003 | Bonnassieux | |
| 6,553,998 B2 | 4/2003 | Heaton et al. | |
| 6,564,803 B2 | 5/2003 | Loefgren | |
| 6,638,605 B1 | 10/2003 | Ankuda, Jr. et al. | |
| 6,694,981 B2 | 2/2004 | Gingles et al. | |
| 6,742,522 B1 | 6/2004 | Baker et al. | |
| 6,764,566 B1 | 7/2004 | Griesbach, III et al. | |
| 6,814,079 B2 | 11/2004 | Heaton et al. | |
| 6,832,611 B2 | 12/2004 | Altman | |
| 6,834,652 B2 | 12/2004 | Altman | |
| 6,875,199 B2 | 4/2005 | Altman | |
| 6,893,422 B2 | 5/2005 | Atlman | |
| 6,936,554 B1 | 8/2005 | Singer et al. | |
| 6,966,081 B1 | 11/2005 | Sharps | |
| 6,978,785 B2 | 12/2005 | Lin | |
| 7,096,870 B2 | 8/2006 | Lamprich et al. | |
| 7,096,871 B2 | 8/2006 | Lee et al. | |
| 7,117,869 B2 | 10/2006 | Heaton et al. | |
| 7,128,753 B1 | 10/2006 | Bonutti et al. | |
| 7,208,013 B1 | 4/2007 | Bonutti | |
| 7,273,054 B2 | 9/2007 | Heaton et al. | |
| 7,275,544 B2 | 10/2007 | Gil et al. | |
| 7,290,547 B2 | 11/2007 | Hare et al. | |
| 7,299,803 B2 | 11/2007 | Kovac et al. | |
| 7,305,991 B2 | 12/2007 | Santilli et al. | |
| 7,409,953 B2 | 8/2008 | Griesbach, III | |
| 7,496,971 B2 | 3/2009 | Soto | |
| 7,533,673 B2 | 5/2009 | Lewis et al. | |
| 7,591,269 B2 | 9/2009 | Small | |
| 7,594,512 B2 | 9/2009 | Reyes et al. | |
| 7,604,007 B1 | 10/2009 | Wooley | |
| 7,610,918 B2 | 11/2009 | Bowen et al. | |
| 7,654,266 B2 | 2/2010 | Corbitt, Jr. | |
| 7,690,380 B2 | 4/2010 | Lee et al. | |
| 7,717,117 B2 | 5/2010 | Duarte | |
| 7,763,060 B2 | 7/2010 | Baumann | |
| 7,828,852 B2 | 11/2010 | Bonutti | |
| 7,837,736 B2 | 11/2010 | Bonutti | |
| 7,856,984 B2 | 12/2010 | Levernier | |
| 7,886,742 B2 | 2/2011 | Haines et al. | |
| 7,886,746 B2 | 2/2011 | Heaton et al. | |
| 7,891,359 B2 | 2/2011 | Corbitt, Jr. et al. | |
| 7,958,894 B2 | 6/2011 | Katoh et al. | |
| 7,981,026 B2 | 7/2011 | Small | |
| 7,992,568 B2 | 8/2011 | Wooley | |
| 7,997,277 B2 | 8/2011 | Reyes et al. | |
| 8,020,561 B2 | 9/2011 | Lee et al. | |
| 8,033,283 B2 | 10/2011 | Lawrentschuk | |
| 8,042,688 B2 | 10/2011 | Parks et al. | |
| 8,079,365 B2 | 12/2011 | Block et al. | |
| 8,100,130 B2 | 1/2012 | Allen et al. | |
| 8,166,977 B2 | 5/2012 | Kovac et al. | |
| 8,281,790 B2 | 10/2012 | Gustafsson et al. | |
| 8,286,637 B2 | 10/2012 | Kaska | |
| 8,371,306 B2 | 2/2013 | Haines et al. | |
| 8,372,129 B2 | 2/2013 | Baumann | |
| 8,424,532 B2 | 4/2013 | Esquivel et al. | |
| 8,491,473 B2 | 7/2013 | Wilson et al. | |
| D693,603 S | 11/2013 | Esquivel et al. | |
| 8,635,725 B2 | 1/2014 | Tannoury et al. | |
| 8,641,694 B2 | 2/2014 | Price et al. | |
| 8,661,580 B2 | 3/2014 | Giap | |
| 8,739,797 B2 | 6/2014 | Bonutti | |
| 8,813,755 B2 | 8/2014 | Hoffmann | |
| 8,826,911 B2 | 9/2014 | Power et al. | |
| 8,826,912 B2 | 9/2014 | Bream, Jr. | |
| 8,827,973 B2 | 9/2014 | Stokes et al. | |
| 8,839,794 B2 | 9/2014 | Tonks et al. | |
| 8,863,747 B1 | 10/2014 | Stephenson | |
| 9,072,646 B2 | 7/2015 | Skripps et al. | |
| D742,140 S | 11/2015 | Esquivel et al. | |
| 9,278,166 B2 | 3/2016 | Czajka, Jr. et al. | |
| 9,351,795 B2 | 5/2016 | Allen et al. | |
| 9,498,397 B2 | 11/2016 | Hight et al. | |
| 9,522,078 B2 | 12/2016 | Pizzini | |
| 9,615,892 B2 | 4/2017 | Piferi et al. | |
| 9,636,180 B2 | 5/2017 | Haines et al. | |
| 9,642,404 B2 | 5/2017 | Giles et al. | |
| 9,687,093 B2 | 6/2017 | Giles et al. | |
| 9,707,040 B2 | 7/2017 | Lager | |
| 9,814,526 B2 | 11/2017 | Sloth et al. | |
| 9,820,751 B2 | 11/2017 | Haines et al. | |
| 9,937,006 B2 | 4/2018 | Skripps et al. | |
| 10,729,507 B2 * | 8/2020 | Beale | A61B 46/40 |
| 2002/0108615 A1 | 8/2002 | Levitt et al. | |
| 2003/0106560 A1 | 6/2003 | Griesbach et al. | |
| 2004/0045557 A1 | 3/2004 | Lee et al. | |
| 2005/0028828 A1 | 2/2005 | Heaton et al. | |
| 2005/0283105 A1 | 12/2005 | Heaton et al. | |
| 2006/0191540 A1 | 8/2006 | Lamprich et al. | |
| 2007/0208378 A1 | 9/2007 | Bonutti et al. | |
| 2008/0047567 A1 | 2/2008 | Bonutti | |
| 2010/0192300 A1 | 8/2010 | Tannoury | |
| 2011/0030702 A1 | 2/2011 | Czajka, Jr. | |
| 2011/0107494 A1 | 5/2011 | Haines | |
| 2012/0111342 A1 | 5/2012 | Lawrentschuk | |
| 2012/0144589 A1 | 6/2012 | Skripps et al. | |
| 2012/0222686 A1 | 9/2012 | Lockwood et al. | |
| 2012/0298115 A1 | 11/2012 | Haines et al. | |
| 2013/0104907 A1 | 5/2013 | Giap | |
| 2013/0152950 A1 | 6/2013 | Giap | |
| 2013/0211425 A1 | 8/2013 | Parsell et al. | |
| 2013/0247921 A1 * | 9/2013 | Dye | A61B 46/00 128/853 |
| 2013/0284187 A1 | 10/2013 | Esquivel et al. | |
| 2014/0137327 A1 | 5/2014 | Tannoury et al. | |
| 2014/0338121 A1 | 11/2014 | Giap | |
| 2015/0044956 A1 | 2/2015 | Hacker | |
| 2015/0272681 A1 | 10/2015 | Skripps et al. | |
| 2016/0135915 A1 | 5/2016 | Czajka, Jr. et al. | |
| 2017/0049651 A1 | 2/2017 | Lim | |
| 2017/0049653 A1 | 2/2017 | Lim | |
| 2017/0112655 A1 | 4/2017 | Giap | |
| 2018/0116891 A1 | 5/2018 | Beale et al. | |
| 2018/0193104 A1 | 7/2018 | Beale et al. | |
| 2018/0289439 A1 | 10/2018 | McGahan et al. | |
| 2018/0363596 A1 | 12/2018 | Lim et al. | |
| 2019/0000702 A1 | 1/2019 | Lim et al. | |
| 2019/0000707 A1 | 1/2019 | Lim et al. | |

(56) References Cited

U.S. PATENT DOCUMENTS

| | | |
|---|---|---|
| 2019/0046381 A1 | 2/2019 | Lim et al. |
| 2019/0046383 A1 | 2/2019 | Lim et al. |
| 2019/0282316 A1 | 9/2019 | Fields et al. |
| 2019/0282317 A1 | 9/2019 | Fields et al. |
| 2019/0282329 A1 | 9/2019 | Hynes |
| 2019/0282330 A1 | 9/2019 | Fields et al. |

FOREIGN PATENT DOCUMENTS

| | | |
|---|---|---|
| CN | 106264736 | 1/2017 |
| EP | 3348224 | 7/2018 |
| JP | 2002-503130 | 1/2002 |
| WO | 9856303 | 12/1998 |
| WO | 2010051303 | 5/2010 |
| WO | 2016102018 | 6/2016 |

OTHER PUBLICATIONS

Japanese Office Action dated Oct. 5, 2021 in from JP2017-246428 and Translation.
Office Action dated Jan. 15, 2021 from Chinese Application No. 201810014366.2.
European Search Report, Surgical Draping System and Method for Using Same, dated Apr. 25, 2018, EP 17209323 Munich, Germany.
International Search Report dated Nov. 21, 2016 from International Application No. PCT/US2016/047394.
Australian Examiner Report dated Jun. 20, 2022 in Australian Application No. 2018200220.

* cited by examiner

SURGICAL DRAPING SYSTEM AND METHOD FOR USING SAME

The present application is a continuation of U.S. application Ser. No. 15/405,090, filed Jan. 12, 2017; all of which is incorporated by reference herein.

BACKGROUND OF THE INVENTION

Field of the Invention

The present invention relates to a surgical draping system and method for using same for facilitating establishment and maintenance for a sterile surgical field around a patient. More particularly, the present invention relates to a surgical draping system and method for using same for facilitating establishment and maintenance of a sterile surgical field even during articulation of a patient using a specialized surgical table. More specifically, the present invention relates to a surgical draping system and method for using same for establishing and maintaining a sterile surgical field even during rotation of a patient by a specialized surgical table.

Description of the Prior Art

A sterile field must be established and maintained during a surgical procedure. A sterile field has traditionally been established and maintained using a conventional sterile surgical drape laid over a patient positioned on a conventional operating room table. The conventional surgical drape generally stays statically positioned over the patient, and is used to establish zones of sterile and non-sterile fields. The space above the surface of the conventional operating table including portions of the conventional surgical drape in this space are considered a sterile field. Furthermore, the space from the surface of the conventional operating table to the floor including portions of the conventional surgical drape in this space are considered a non-sterile field.

Simultaneous access spinal procedures have become more common. During such procedures, for example, a posterior portion of the patient and a lateral side of the patient can be accessed, or an anterior portion of the patient and a lateral side of the patient can be accessed. Specialized surgical tables for repositioning and/or manipulating the patient have been provided to facilitate the simultaneous access spinal procedures. During a simultaneous access spinal procedure, the surgical site or sites must remain sterile during any repositioning and/or manipulation of the patient. However, if, for example, the patient is rotated using a specialized surgical table, portions of the patient and the draping covering the patient may pass into the non-sterile field. Therefore, there is a need for a surgical draping system and method for using same for facilitating the establishment and maintenance of a surgical field around a surgical site or sites even during articulation of the patient during surgery. To illustrate, the surgical draping system and method for using same can be used to maintain a sterile field around a surgical site or sites during rotation of the patient.

SUMMARY OF THE INVENTION

The present invention in one preferred embodiment contemplates a surgical draping system for creating a sterile surgical corridor to at least two surgical sites on a patient during articulation of the patient with a surgical table positioned on an operating room floor, the surgical draping system including an under-draping configured for positioning over the patient, a portion of the under-draping being capable of being maintained in a substantially static position with respect to the patient, the portion of the under-draping including a first aperture therethrough, the first aperture being sized to afford access to the at least two surgical sites on the patient, an over-draping configured for positioning over the under-draping and the patient, a portion of the over-draping being capable of being maintained in a substantially static position with respect to the operating room floor, the over-draping including a second aperture therethrough, the second aperture being sized to afford access to the at least two surgical sites on the patient, a connecting draping configured for attachment between the under-draping and the over-draping, the connecting draping being expandable and contractible between a first position and a second position, the connecting draping including a first end, a second end, a third aperture formed at the first end, a fourth aperture formed at the second end, and an enclosed passageway therethrough from the third aperture at the first end to the fourth aperture at the second end, the first end being attachable around the first aperture of the under-draping and the second end being attachable around the second aperture of the under-draping to create the sterile surgical corridor through the enclosed passageway between the first aperture of the under-draping and the second aperture of the over-draping to afford access to the at least two surgical sites, where, when the under-draping is positioned over the patient, the over-draping is positioned over the under-draping and the patient, and the connecting draping is attached to the under-draping and the over-draping to afford access to the at least two surgical sites through the sterile surgical corridor, the patient is articulable on the surgical table, and portions of the connecting draping expands and contracts to maintain access to the at least two surgical sites through the sterile surgical corridor enclosed passageway.

The present invention in another preferred embodiment contemplates a method of establishing and maintaining a sterile surgical corridor to at least two surgical sites on a patient during articulation of a surgical table positioned on an operating table floor, the method including positioning the patient on the surgical table positioned on the operating table floor, positioning an under-draping over the patient so that a first aperture therethrough is positioned over at least two surgical sites on the patient, the first aperture being sized to afford access to the at least two surgical sites, maintaining portions of the under-draping in a substantially static position with respect to the patient, positioning an over-draping over the under-draping and the patient so that a second aperture therethrough is positioned over the first aperture, the second aperture being sized to afford access to the at least two surgical sites, attaching a connecting draping having an enclosed passageway therethrough between a first end and a second end thereof between the under-draping and the over-draping by attaching the first end and a third aperture formed at the first end around the first aperture of the under-draping, and by attaching the second end and a fourth aperture formed at the second end around the second aperture of the over-draping so that a sterile surgical corridor is formed to the at least two surgical sites through the over-draping, the connecting draping, and the under-draping, articulating the position of the patient using the surgical table, and maintaining the sterile surgical corridor through the over-draping, the connecting draping, and the under-draping during articulation of the patient using the surgical table.

The present invention in yet another preferred embodiment contemplates a method of establishing and maintaining a sterile surgical corridor to at least two surgical sites on a patient during articulation of a surgical table positioned on an operating table floor, the method including positioning an under-draping over the patient positioned on the surgical table, aligning a first aperture formed through the under-draping over the at least two surgical sites on the patient to provide access thereto, positioning an over-draping over the under-draping and the patient, attaching a connecting draping having a first end with a third aperture, a second end with a fourth aperture, and an enclosed passageway therethrough between the third and fourth apertures to the under-draping and the over-draping by attaching the first end and the third aperture around the first aperture of the under-draping and attaching the second end and the fourth aperture around a second aperture formed through the over-draping to form the sterile surgical corridor through the over-draping, the connecting draping, and the under-draping, articulating the position of the patient using the surgical table, and maintaining the sterile surgical corridor through the over-draping, the connecting draping, and the under-draping during articulation of the patient using the surgical table.

These and other objects of the present invention will be apparent from review of the following specification and the accompanying drawings.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings.

DETAILED DESCRIPTION OF THE PREFERRED EMBODIMENT

Figure 1:
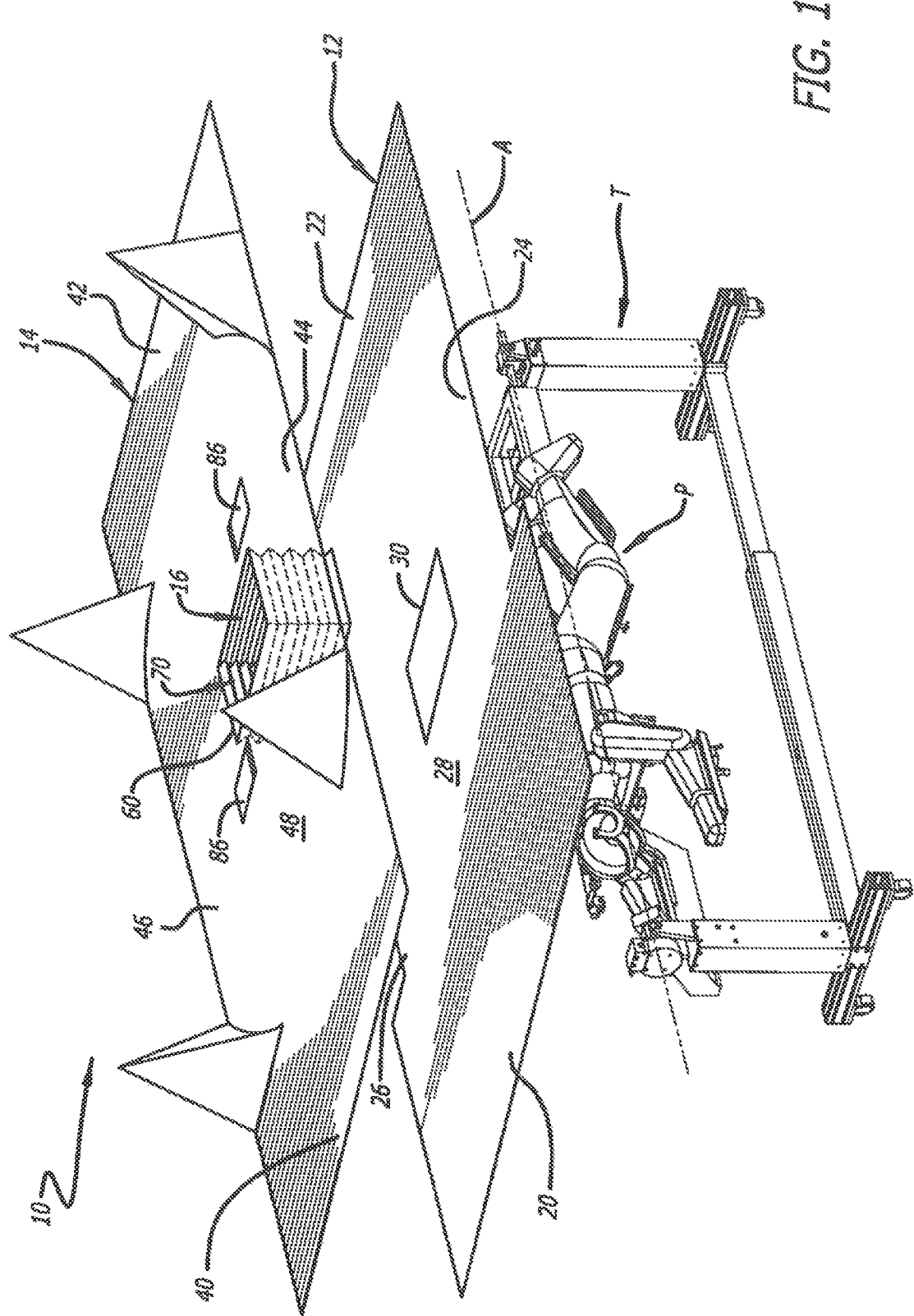
FIG. 1 is an exploded perspective view of a draping system including an under-draping, an over-draping, and a connecting draping for facilitating establishment and maintenance of a sterile surgical corridor to a surgical site or sites on a patient supported by a surgical table.
Figure 8:
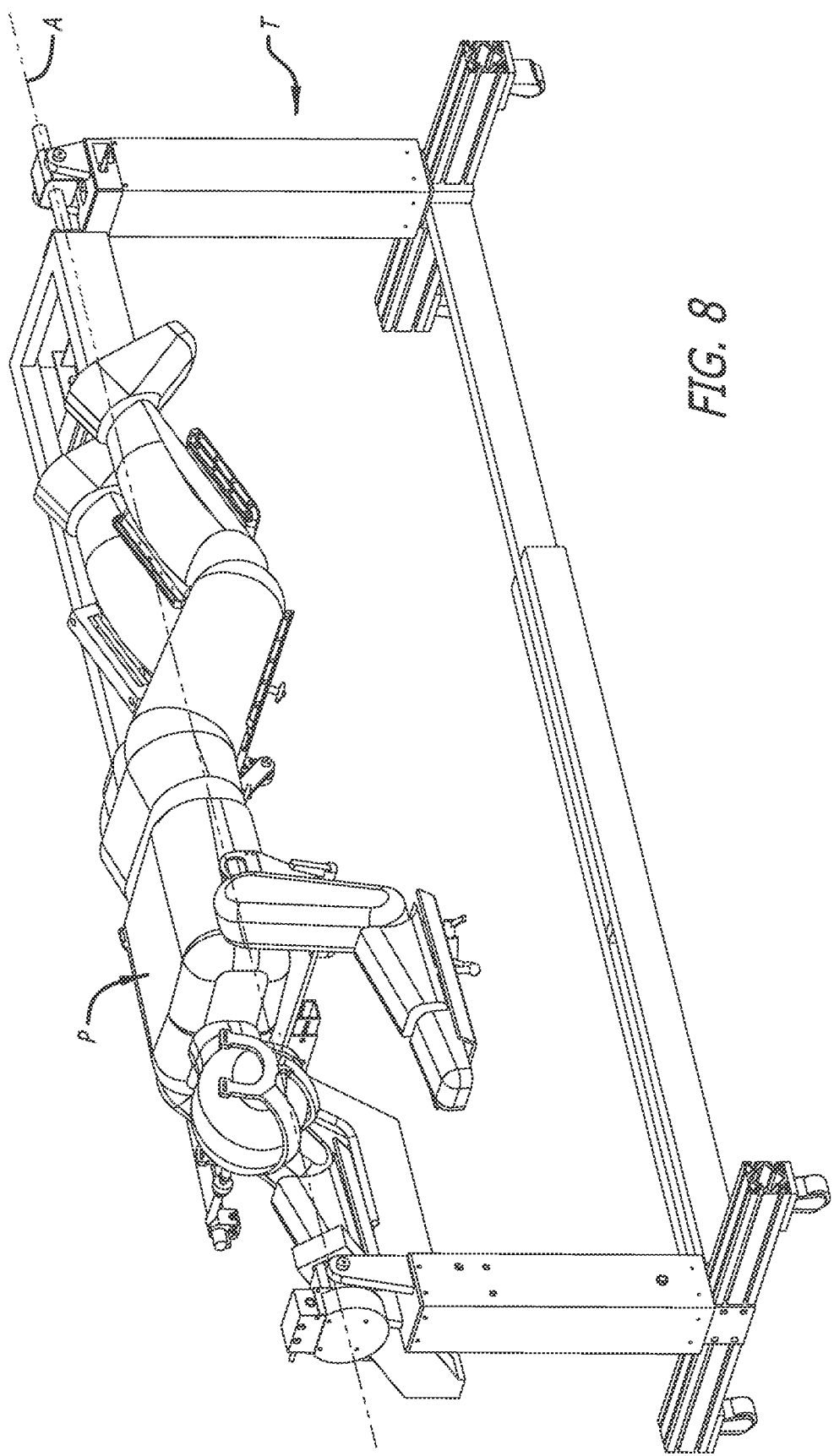
FIG. 8 is a top perspective view of a surgical table with the patient positioned thereon in a prone position.
Figure 9:
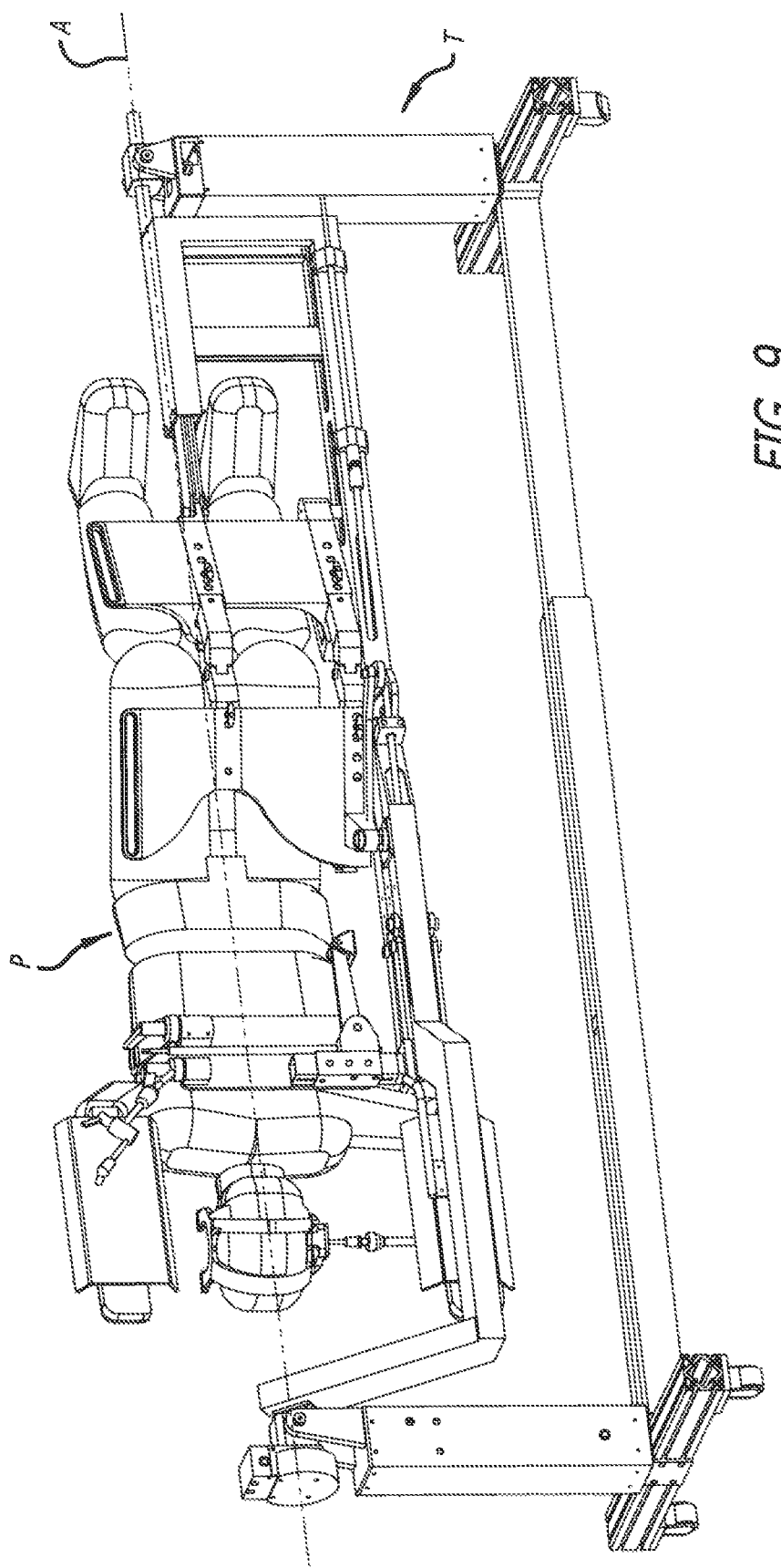
FIG. 9 is a top perspective view of the surgical table of FIG. 8 with the patient positioned thereon in a lateral position.

A surgical draping system according to the present invention is generally referenced by the numeral 10 in FIGS. 1, 4, and 12-15, and portions of the surgical draping system are depicted in FIGS. 2, 3, 5-7, 10, and 11. The surgical draping system 10 can be used in conjunction with a surgical table T, as depicted in FIGS. 1, 8, and 9, capable of articulating the position of a patient P during surgery.

Such a surgical table T is disclosed in U.S. application Ser. No. 15/239,256, filed Aug. 17, 2016, which is hereby incorporated by reference herein. The surgical table T is capable of rotating the patient P about an axis of rotation A. The articulation of the patient P using the surgical table T can be used to facilitate performance of simultaneous access spinal procedures. For example, such simultaneous access spinal procedures can include accessing one of a right lateral side portion and a left lateral side portion, and one of an anterior portion and a posterior portion of the patient P.

A sterile field must be established and maintained during a surgical procedure. Traditionally, a sterile field is established and maintained at and above the surface of a conventional operating table using a conventional surgical drape. The surface of a conventional operating table usually corresponds to the height of a surgeon's waist. The space above the surface of the conventional operating table including portions of the conventional surgical drape in this space are considered a sterile field. Furthermore, the space from the surface of the conventional operating table to the floor including portions of the conventional surgical drape in this space are considered a non-sterile field. Given that the surgical table T is capable of articulating the patient P, portions of the patient (including a surgical site or sites and the space therearound) and portions of the conventional surgical drape could potentially pass from the sterile field into the non-sterile field below the height of a surgeon's waist during and after such rotation.

The draping system 10 is provided to establish and maintain a sterile field around the surgical site or sites and area around the surgical site or sites even during articulation of the patient P by the surgical table T. For example, the draping system 10 can be used to establish and maintain a sterile surgical corridor 11 to the surgical site or sites even during articulation of the patient P using the surgical table T.

As such, the patient P, for example, can be rotated by the surgical table T from a lateral position to a prone position, or vice versa, and the surgical draping system 10 serves in maintaining a surgical field around the surgical site or sites and area around a surgical site or sites during such rotation.

The surgical draping system 10 includes under-draping 12, over-draping 14, and connecting draping 16. The under-draping 12, the over-draping 14, and the connecting draping 16 each can be formed from a single sheet of material or multiple sheets of material attached together. The under-draping 12, the over-draping 14, and the connecting draping 16 are made from materials suitable for use as surgical drapes. As discussed below, the under-draping 12 is positioned to directly contact the patient P, the over-draping 14 is positioned over the under-draping 12, and the connecting draping 16 connects portions of the under-draping 12 and the over-drawing 14 to one another. The sterile surgical corridor 11 is provided through the over-draping 14, through the connecting draping 16, and through the under-draping 12.

As depicted in FIGS. 1 and 8-12, the patient P is positioned on the surgical table T, and the surgical table T is capable of articulating the patient P thereon, i.e., the surgical table T is capable of rotating the patient P from a prone position (FIG. 8) to a lateral position (FIG. 9), and is capable of rotating the patient P from the lateral position (FIG. 9) to the prone position (FIG. 8).

Figure 7:
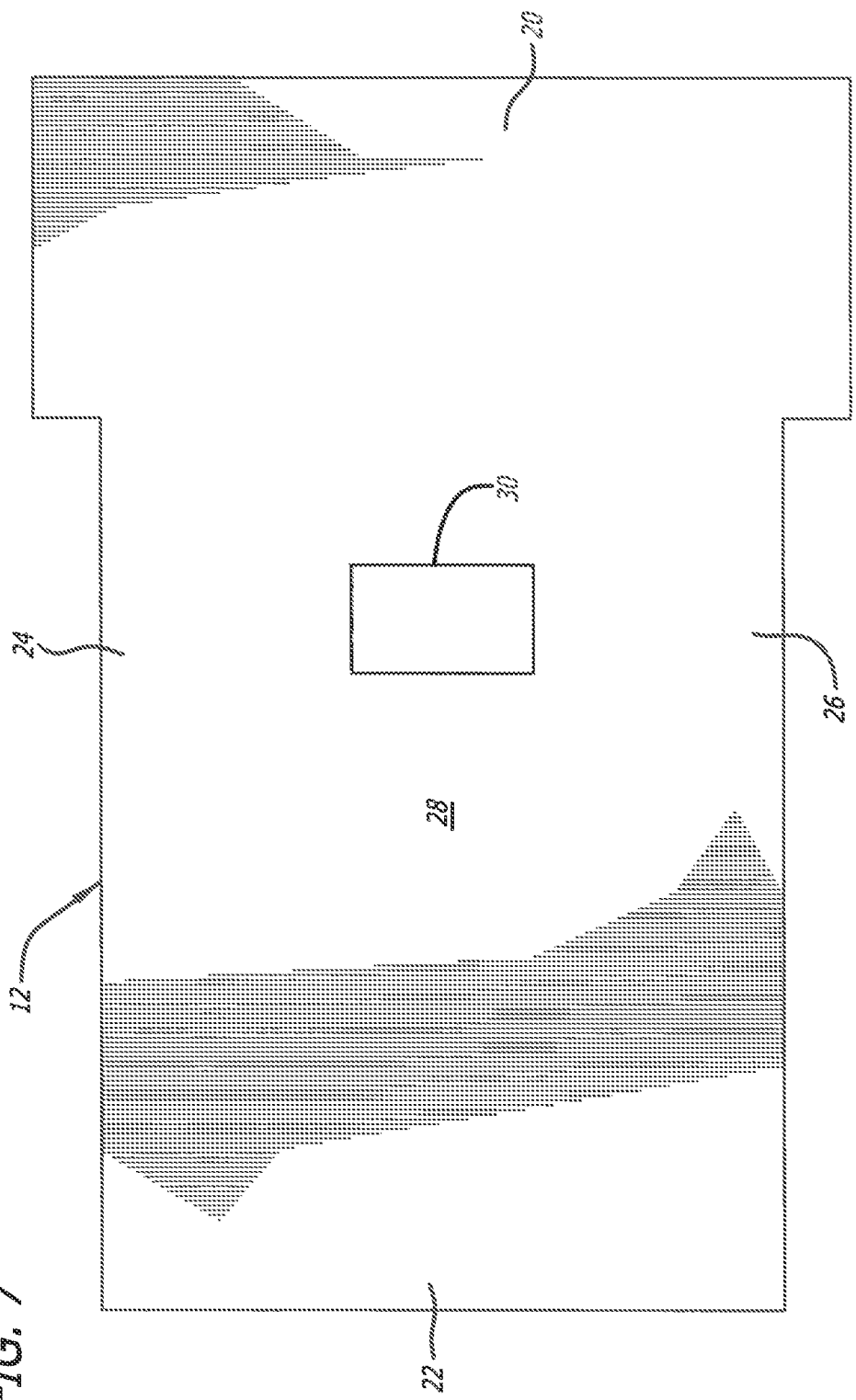
FIG. 7 is a top plan view of the under-draping laid flat.
Figure 10:
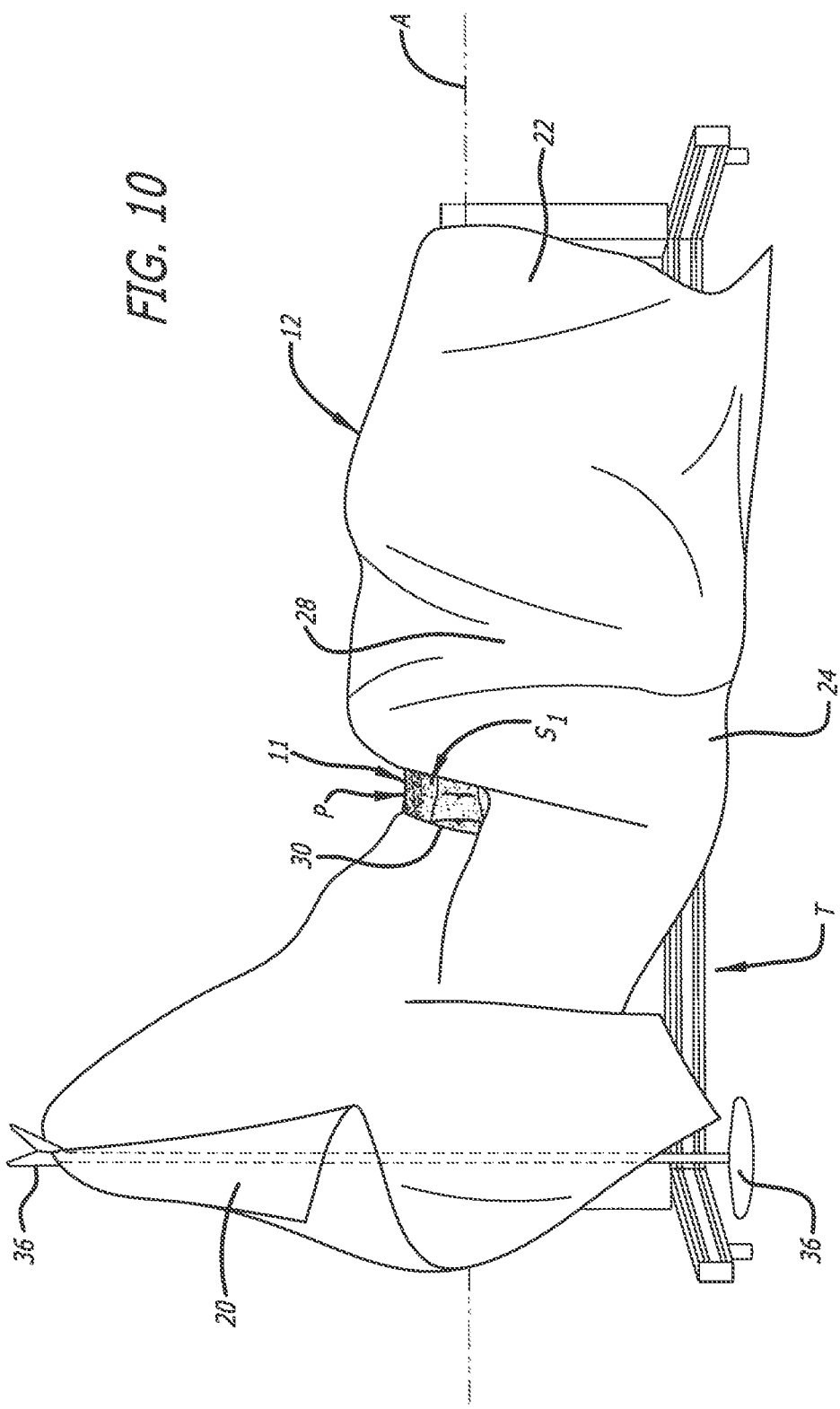
FIG. 10 is a side perspective view of the under-draping positioned over the patient supported by the surgical table of FIGS. 8 and 9 in a lateral position.
Figure 11:
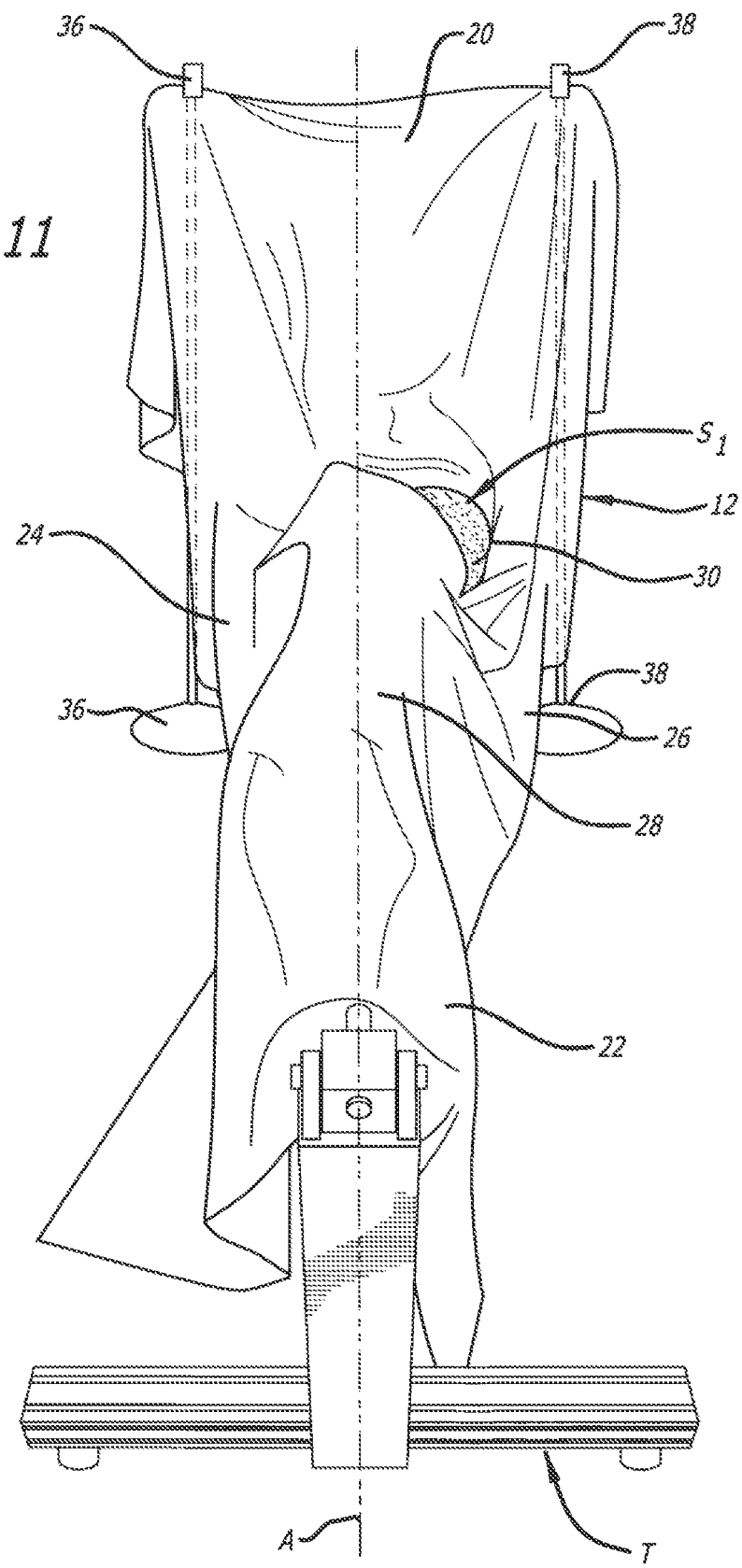
FIG. 11 is an end perspective view of the under-draping positioned over the patient supported by the surgical table of FIGS. 8 and 9 in a lateral position.

The under-draping 12, as depicted in FIGS. 1, 7, 10, and 11, includes a cranial end 20, a caudal end 22, a first lateral side 24, a second lateral side 26, and a body portion 28. The body portion 28 is positioned between the cranial end 20, the caudal end 22, and the first and second lateral sides 24 and 26. As their names suggest, the cranial end 20 is positioned on the upper portion of the patient P (FIGS. 10 and 11), and the caudal end 22 is positioned on the lower portion of the patient P (FIGS. 10 and 11). The first and second lateral sides 24 and 26 extend between the cranial end 20 and the caudal end 22. When, as depicted in FIG. 7, the under-draping 12 is laid upon a flat surface, the under-draping 12 is generally rectangular. However, the under-draping 12 can have any number of shapes provided that it is large enough to cover all or parts of the surgical table T, and all or parts of the patient P.

As depicted in FIGS. 10 and 11, large portions of the under-draping 12 (including the body portion 28) are positioned to directly contact and cover the patient P. As such, large portions of the under-draping 12 are positioned statically with respect to the patient P. Other portions of the under-draping 12 at the cranial end of the patent P are supported by support stands 36 and 38. Support the under-draping 12 by the support stands 36 and 38 afford access to the head of the patient P.

The under-draping 12 includes an aperture 30 formed through the body portion 28 for positioning over at least two surgical sites on the patient P. The aperture 30 can be one or more apertures, and can have any size and shape so long as access is provided to at least two surgical sites therethrough. For example, the aperture 30 could have generally digonal, polygonal, circular, oval, elliptical, cross, etc. shapes. The aperture 30 can be sized and shaped to, for example, provide access to one of a right lateral side portion and a left lateral side portion of the patient, and one of an anterior portion and a posterior portion of the patient P.

As depicted in FIG. 7, the aperture 30 has a rectangular shape, and, when the aperture 30 is positioned over the at least two surgical sites (FIGS. 10 and 11), the aperture 30 is oriented such that the long axis thereof extends in a direction transverse to the axis of rotation A. As discussed above, the aperture 30 can be sized and shaped such that it extends from a surgical site affording access to a posterior side of the patient P to a surgical site affording access to a lateral side of the patient P, or extends from a surgical site affording access to an anterior side of the patient P to a surgical site affording access to a lateral side of the patient P.

The aperture 30 could also be sized to extend from one lateral side to the other lateral side of the patient P across either the posterior side or the anterior side of the patient P. As such, the aperture 30 could be sized to afford access to three surgical sites: a first lateral surgical site on one side of the patient P, a second lateral surgical site on the other side of the patient P, and a third surgical site on either the posterior side or the anterior side of the patient P.

The rectangular-shaped aperture 30 can also be oriented such that the long axis thereof extends in a direction aligned with the axis of rotation A. As such, the rectangular-shaped aperture 30 could be positioned to extend along the spine of the patient P to afford access to different surgical sites along the spine.

The aperture 30 can also be sized and shaped as a cross. The cross-shaped aperture 30 can include two long axes such that a first of the long axes extends in a direction transverse to the axis of rotation A, and a second of the long axes extends in a direction aligned with the axis of rotation A. As such, the first of the long axes can extend from a surgical site affording access to a posterior side of the patient P to a surgical site affording access to a lateral side of the patient P, or extend from a surgical site affording access to an anterior side of the patient P to a surgical site affording access to a lateral side of the patient P. Furthermore, the second of the long axes can extend along the spine of the patient P to afford access to different surgical sites along the spine.

Figure 2:
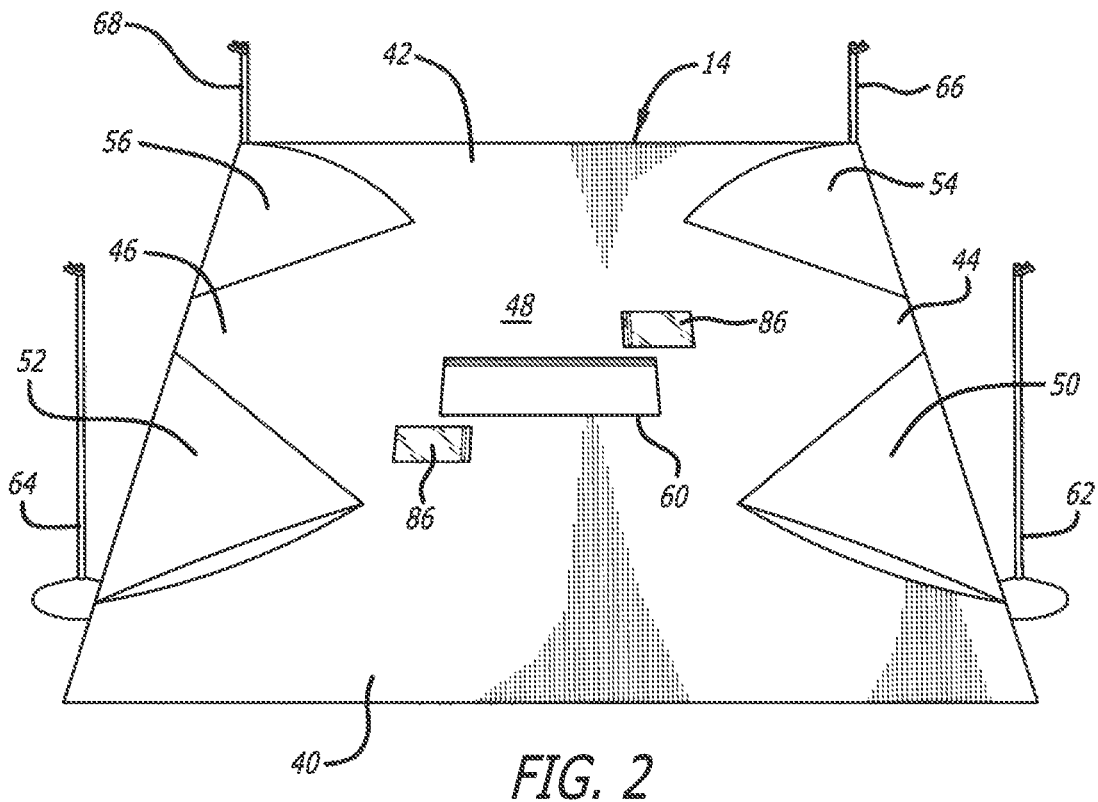
FIG. 2 is a first perspective view of a majority of the over-draping laid flat showing extensions formed in the over-draping folded over onto the over-draping.
Figure 3:
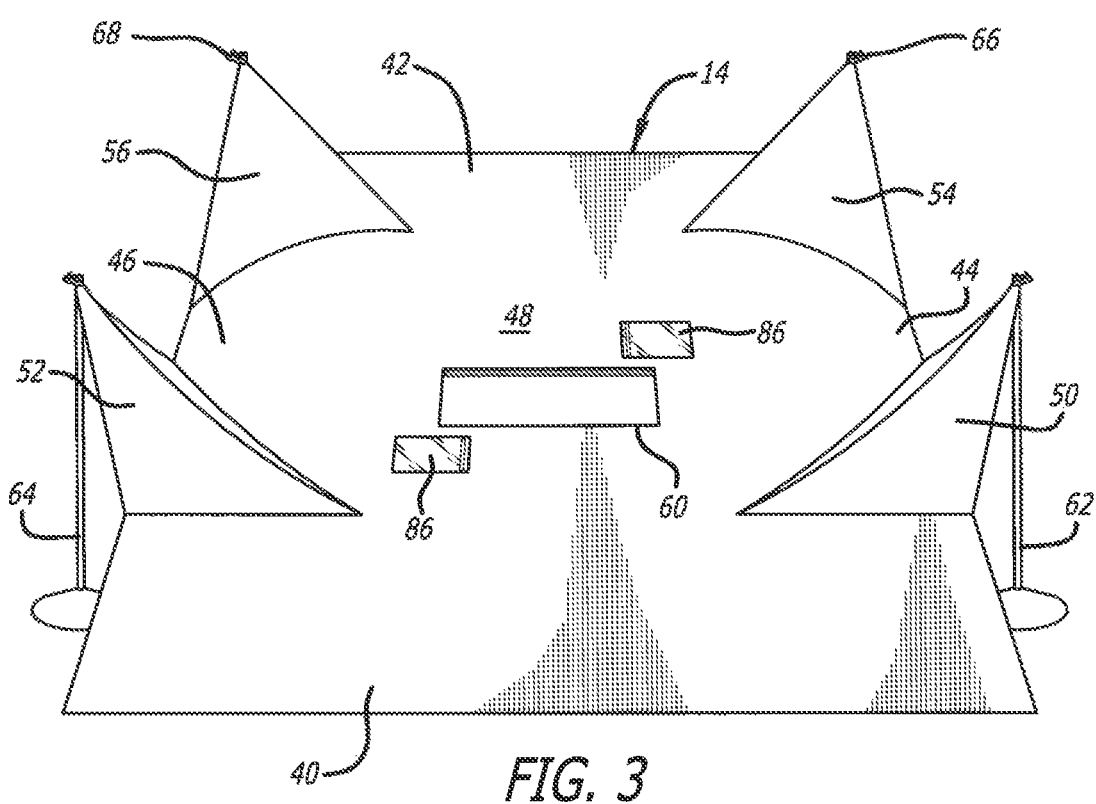
FIG. 3 is a second perspective view of a majority of the over-draping laid flat showing the extensions formed in the over-draping expanded.

The over-draping 14, as depicted in FIGS. 1-3 and 12, includes a cranial end 40, a caudal end 42, a first lateral side 44, a second lateral side 46, and a body portion 48. The body portion 48 is positioned between the cranial end 40, the caudal end 42, and the first and second lateral sides 44 and 46. As their names suggest, the cranial end 40 is positioned adjacent the upper portion of the patient P, and the caudal end 42 is positioned adjacent the lower portion of the patient P. The first and second lateral sides 44 and 46 extend between the cranial end 40 and the caudal end 42. When, as depicted in FIGS. 2 and 3, the over-draping 14 is laid upon a flat surface, the over-draping 14 is generally rectangular. However, the over-draping 14 can have any number of shapes provided that it is large enough to cover all or parts of the under-draping 12, all or parts of the surgical table T, and all or parts of the patient P.

The over-draping 14 can have a plurality of extensions that afford a variety of three-dimensional shapes for the over-draping 14 when the over-draping 14 is positioned over the under-draping 12. As discussed below, portions of the over-draping 14 are hung over the under-draping 12, the surgical table T, and the patient P. For example, the over-draping can include a first extension 50 and a second extension 52 along the cranial end 40, and a third extension 54 and a fourth extension 56 along the caudal end 42. The plurality of extensions could also be provided along the first and second lateral sides 44 and 46.

As depicted in FIGS. 2 and 3, the extensions 50, 52, 54, and 56 could be formed as pleatings provided in the remainder of over-draping. As such, the extensions 50, 52, 54, and 56 can each be formed from an additional amount of material formed or inserted into the remainder of the over-draping 14. This additional amount of material for each of the extensions 50, 52, 54, and 56 exhibits as material folded over onto itself when the over-draping 14 is laid upon a flat surface, as depicted in FIG. 2. As discussed below, portions of the extensions 50, 52, 54, and 56 are attached to and supported at heights above the under-draping 12, the surgical table T, and the patient P, and support stands 62, 64, 66, and 68 (FIGS. 2 and 3) can be used for such support. The slack in the over-draping 14 afforded by the extensions 50, 52, 54, and 56 allow for articulation of the patient P and the under-draping 12 by the surgical table T thereunder without pulling the over-draping 14 down from the support stands 62, 64, 66, and 68.

Rather than being formed as pleatings, the extensions 50, 52, 54, and 56 could be formed from additional amounts of material provided at the cranial end 40 and the caudal end 42 afforded by the shape the over-draping 14. For example, when laid upon a flat surface, the first and second lateral sides 44 and 46 could taper from both the cranial end 40 and the caudal end 42 toward the middle of the over-draping 14. As such, the over-draping 14 could have an "hourglass" shape with more material provided adjacent the cranial end 40 and the caudal end 42, than adjacent the middle of the over-draping 14. Portions of the additional material forming the extensions 50, 52, 54, and 56 could then be attached to and supported at heights above the under-draping 12, the surgical table T, and the patient P using the support stands 62, 64, 66, and 68.

By attaching and supporting portions of the extensions 50, 52, 54, and 56 of the over-draping 14 at heights above the under-draping 12, the surgical table T, and the patient P, large portions of the over-draping 14 can remain in a semi-static position with respect to the operating room floor as the patient P and the under-draping 12 is articulated by the surgical table T. That is, because the over-draping 14 is effectively hung using the extensions 50, 52, 54, and 56 at heights above the under-draping 12, the surgical table T, and the patient P using the support stands 62, 64, 66, and 68, large portions of the over-draping 14 (including the body portion 48) can remain largely in position as the patient P and the under-draping 12 is articulated by the surgical table T.

The extensions 50, 52, 54, and 56 are attached to the support stands 62, 64, 66, and 68, respectively. The support stands 62, 64, 66, and 68 are positioned around the surgical table T with the support stands 62 and 64 being positioned adjacent the cranial end of the patient P and adjacent the cranial end 40 of the over-draping 14, and the support stands 66 and 68 being positioned adjacent the caudal end of the patient P and adjacent the caudal end 42 of the over-draping 14. The heights of the support stands 62, 64, 66, and 68 can be adjustable upwardly and downwardly, and the upper portions thereof include attachment mechanisms for attaching the extensions 50, 52, 54, and 56 thereto. By attaching the extensions 50, 52, 54, and 56 to the support stands 62, 64, 66, and 68, respectively, the body portion 48 of the over-draping 14 can be hung therebetween. Furthermore, while the extensions 50, 52, 54, and 56 are attached directly to the support stands 62, 64, 66, and 68, straps (not shown) attached to portions of the extensions 50, 52, 54, and 56 and/or other portions of the over-drape 14 can be used in attaching the over-draping 14 to the support stands 62, 64, 66, and 68.

As depicted in FIGS. 1, 4, and 12-15, portions of the over-draping 14 (including the body portion 48) are positioned above the aperture 30 formed in the under-draping 12. The over-draping 14 includes an aperture 60 formed through the body portion 48 for positioning over the aperture 30 and the at least two surgical sites. The aperture 60 can be one or more apertures, and can be sized, shaped, and oriented to correspond to the size and shape of the aperture 30. For example, like the aperture 30, the aperture 60 can have generally digonal, polygonal, circular, oval, elliptical, cross, etc. shapes.

As depicted in FIGS. 1-3, the aperture 60 has a rectangular shape corresponding to the rectangular-shaped aperture 30, and when the aperture 60 is positioned over the aperture 30 and at least two surgical sites, the aperture 60 is oriented such that the long axis thereof extends in a direction oriented with the long axis of the aperture 30. If the aperture 30 is sized and shaped to extend from a surgical site affording access to a posterior side of the patient P to a surgical site affording access to a lateral side of the patient P, extend from a surgical site affording access to an anterior side of the patient P to a surgical site affording access to a lateral side of the patient P, or extend from a surgical site on one lateral side to a surgical site on the other lateral side of the patient P across either the posterior side or the anterior side of the patient P, the aperture 60 is sized, shaped, and oriented accordingly. Furthermore, the aperture 60 would similarly be sized, shaped, and oriented to correspond to the aperture 30 if the aperture 30 is cross-shaped.

The apertures 30 and 60 are interconnected with one another using the connecting draping 16. The connecting draping 16 forms an enclosed passageway 70 between the apertures 30 and 60, and the connecting draping 16 is capable of expanding and contracting. The aperture 60, the enclosed passageway 70, and the aperture 30 form the sterile surgical corridor 11 to the surgical site or sites. As such, given that the patient P and the under-draping 12 can be articulated relative to the over-draping 14 using the surgical table T, the enclosed passageway 70 (and hence, the sterile surgical corridor 11) can change its orientation to accommodate the articulation of the patient P and under-draping 12. In other words, the capability of expansion and contraction of the connecting draping 16 allows the connecting draping 16 to change its shape as the patient P and the under-draping 12 are moved relative to the over-draping 14. For example, during rotation of the patient P and the under-draping 12, the connecting draping 16 would articulate to maintain access to the surgical site or sites via the sterile surgical corridor 11 formed by the aperture 60, the enclosed passageway 70, and the aperture 30.

Figure 12:
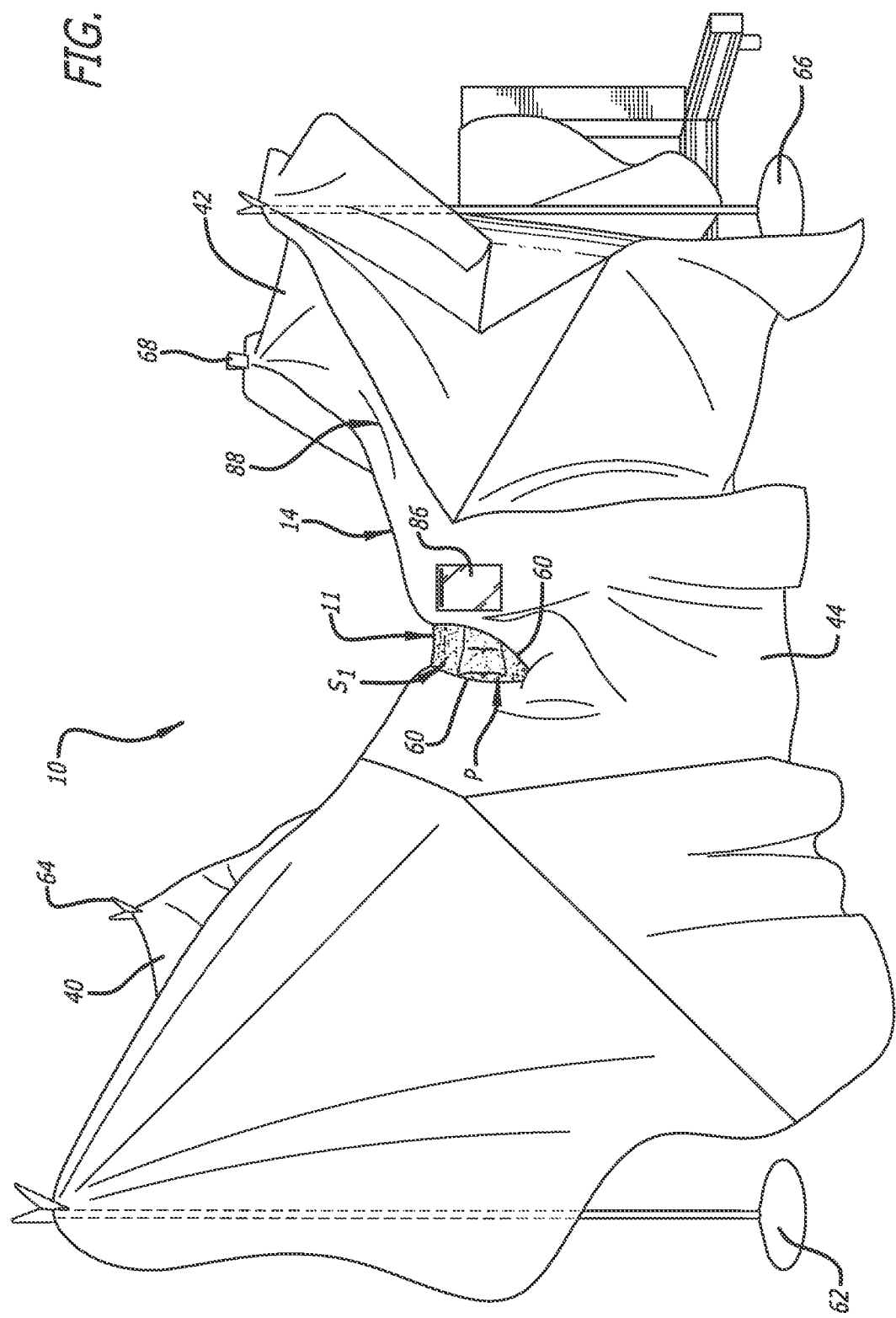
FIG. 12 is a side perspective view of the over-draping positioned over the under-draping and the patient to define the sterile surgical corridor to the surgical site or sites on the patient supported by the surgical table of FIGS. 8 and 9 in a lateral position.
Figure 13:
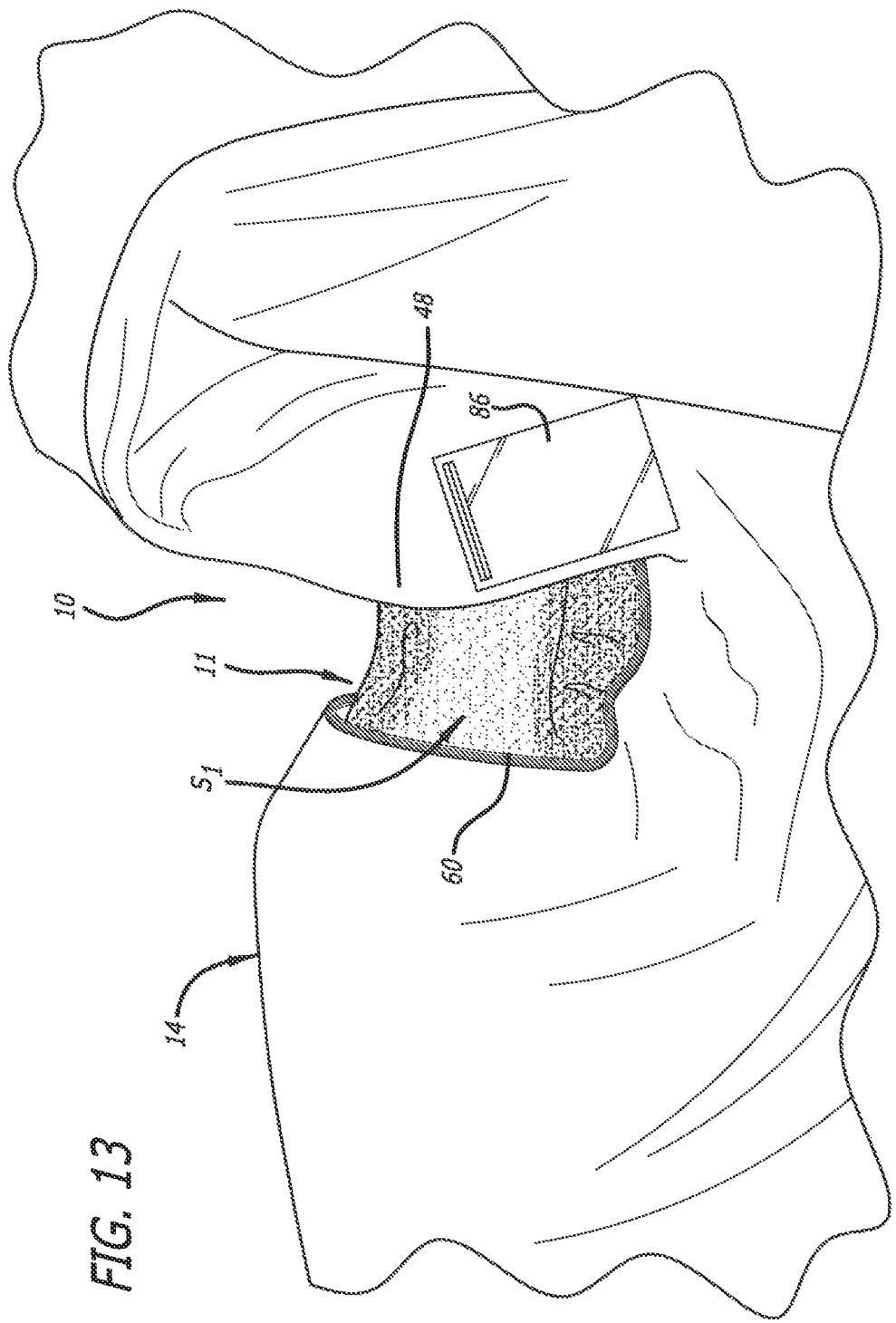
FIG. 13 is an enlarged side fragmentary perspective view from the opposite side shown in FIG. 12 depicting access to the surgical site or sites through the sterile surgical corridor with the connecting draping in an unexpanded position with patient in a lateral position.
Figure 14:
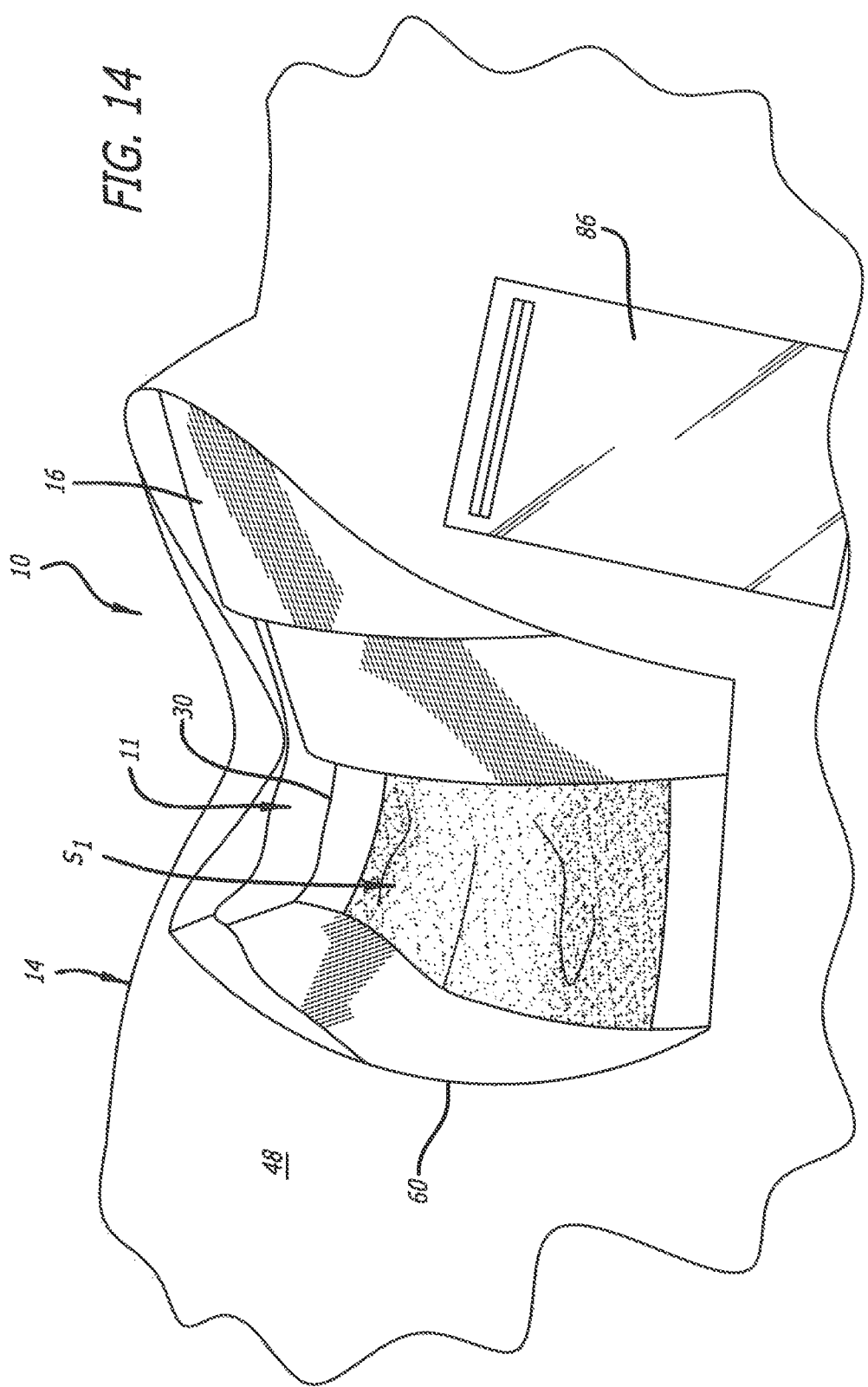
FIG. 14 is an enlarged top side fragmentary perspective view from the side shown in FIG. 12 also depicting access to the surgical site or sites through the sterile surgical corridor with the connecting draping in an expanded position with the patient in a lateral position.
Figure 15:
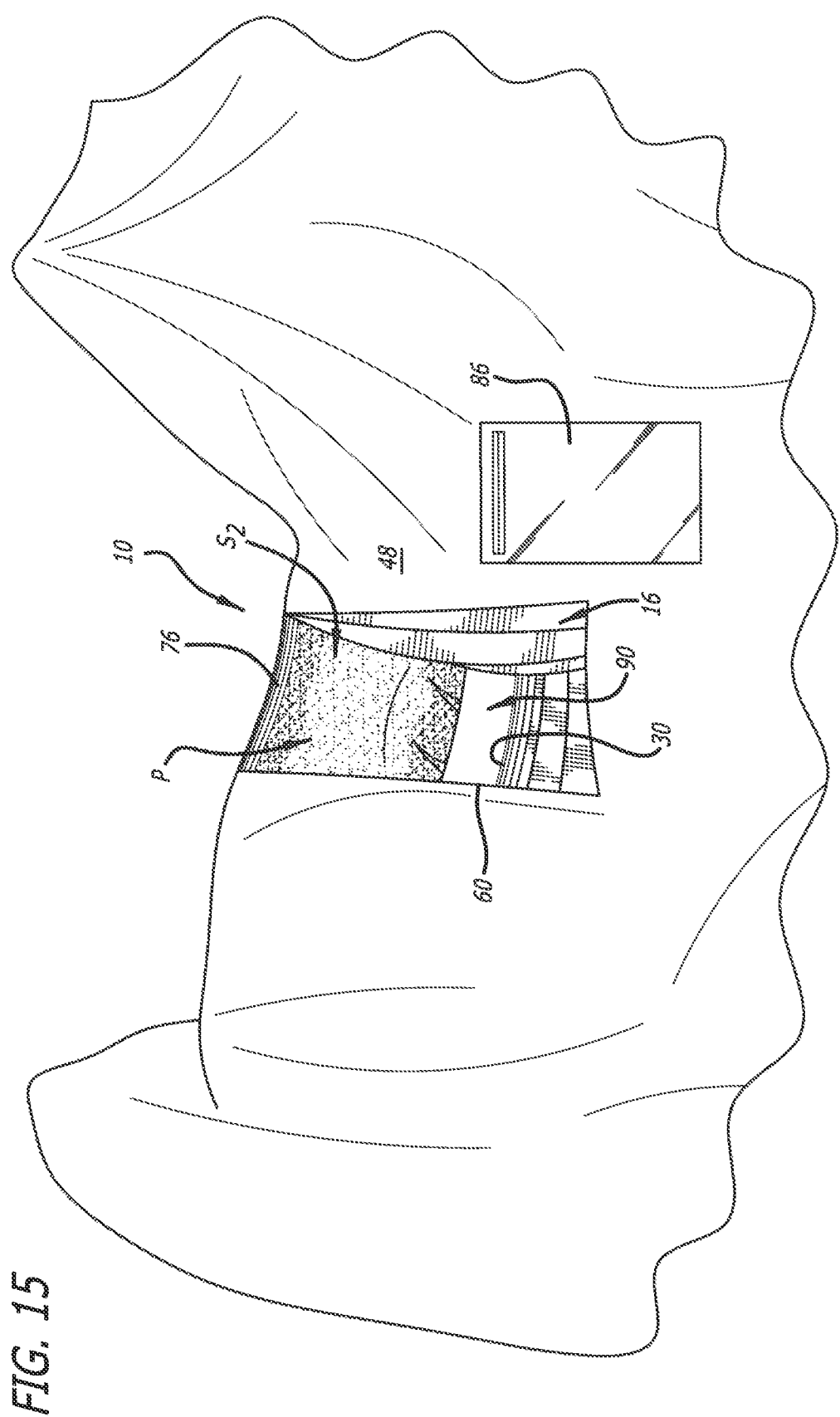
FIG. 15 is a an enlarged side fragmentary perspective view from the side shown in FIG. 12 depicting the access to the surgical site or sites through the sterile surgical corridor after the patient has been repositioned using the surgical table of FIGS. 8 and 9 from a lateral position (FIGS. 12-14) to a prone position.

As depicted in FIGS. 12-14, access by a surgeon is provided to a first surgical site $S_1$, when the patient P is supported in a lateral position by the surgical table T. As discussed above, the apertures 30 and 60 are sized and shaped to also provide access to a second surgical site $S_2$, as depicted in FIG. 15. FIG. 15 depicts the patient P supported in a prone position by the surgical table T. Rotation of the patient P and the under-draping 12 away from a position for accessing the first surgical site $S_1$ in FIGS. 12-14 causes the connecting draping 16 to expand in order to adjust to the rotation. As depicted in FIG. 15, such adjustment serves providing access to the second surgical site $S_2$ to access by a surgeon, while still maintaining a sterile surgical corridor 11 through the aperture 60, the enclosed passageway 70, and the aperture 30. Furthermore, given the rotation of the patient P from a lateral position (FIGS. 12-14) to a prone position (FIG. 15), the sterile surgical corridor 11 through the aperture 60, the enclosed passageway 70, and the aperture 30 creates access to an area 90 underneath the patient P. Access to a position underneath the patient P such as the area 90 was typically not available during surgery.

As discussed above, a sterile field must be established and maintained during a surgical procedure, and a sterile field is established and maintained at and above the surface of a conventional operating table. The surgical draping system 10 afford establishment and maintenance of the sterile surgical corridor, even when the patient P and under-draping 12 are articulated by the surgical table T. As discussed above, the under-draping 12 is positioned to directly contact the patient P, and the aperture 30 provides access to at least two surgical sites. The area around the at least two surgical sites is in the sterile field established by use of the under-draping 12. Furthermore, as discussed above, the over-draping 14 is effectively hung at heights above the under-draping 12, the surgical table T, and the patient P. The sterile field is also established by the over-draping 14. However, when the patient P is rotated by the surgical table T, one or more of the surgical sites could potentially pass into the non-sterile field below the height of a surgeon's waist. Use of the connecting draping 16 facilitates establishment and maintenance of the sterile surgical corridor 11 via the aperture 60, the enclosed passageway 70, and the aperture 30 even if one or more of the surgical sites pass below the height of a surgeon's waist.

Figure 4:
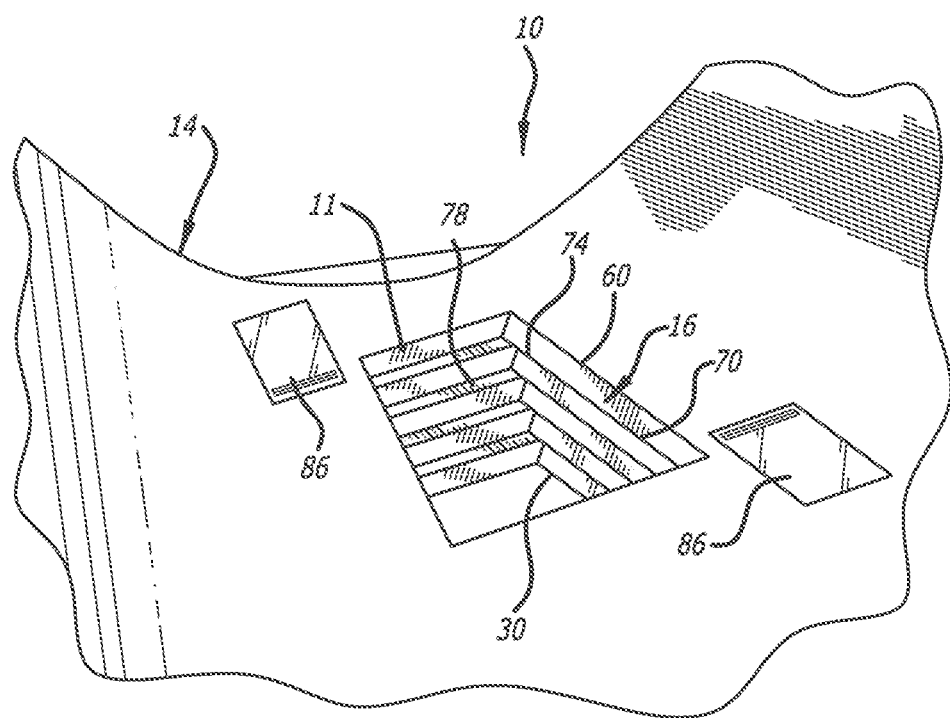
FIG. 4 is a perspective fragmentary view showing an aperture formed in the over-draping and the connecting draping partially expanded underneath the aperture formed in the over-draping.
Figure 5:
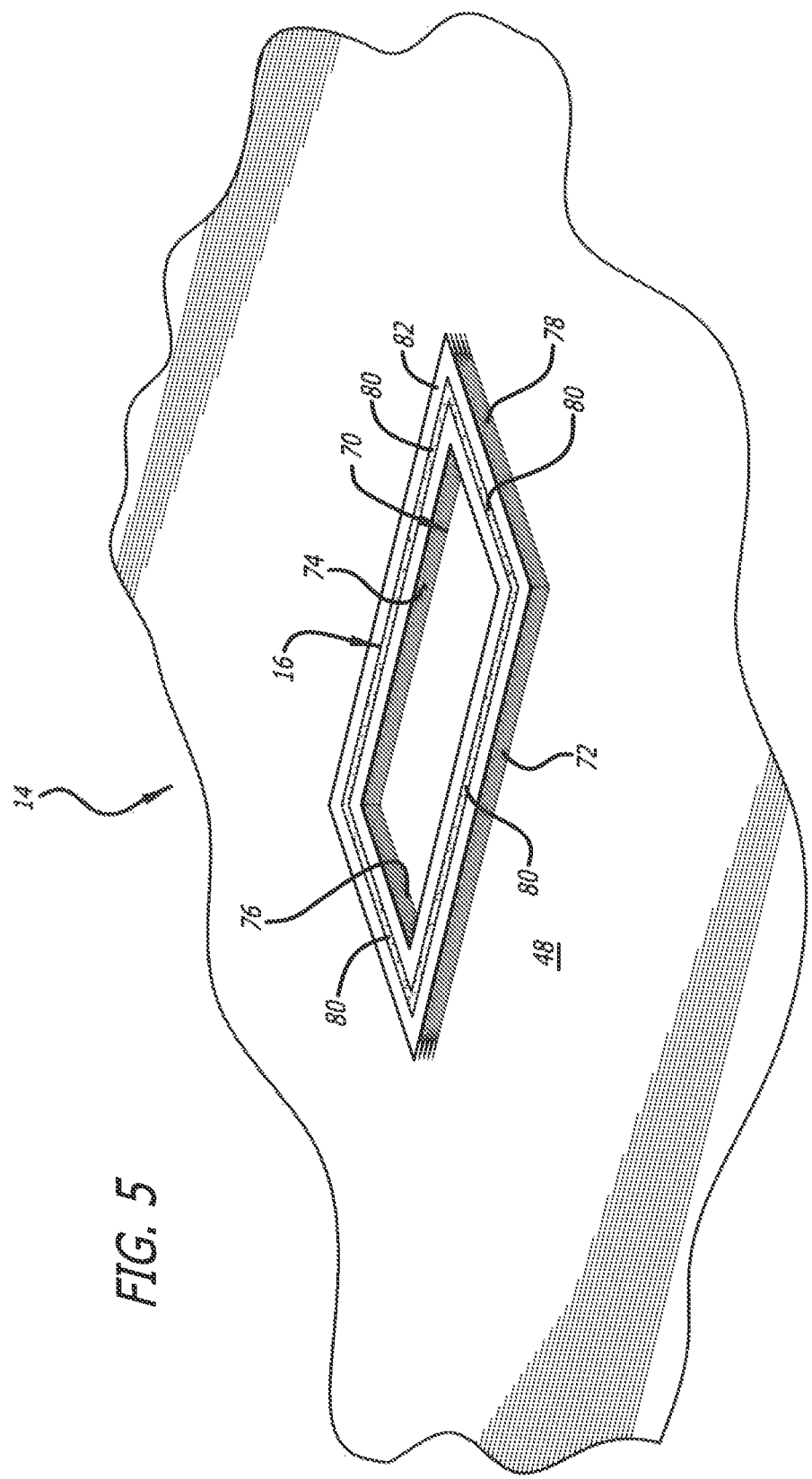
FIG. 5 is a perspective fragmentary view of the bottom of the over-draping and the connecting draping showing the connecting draping in an unexpanded position.
Figure 6:
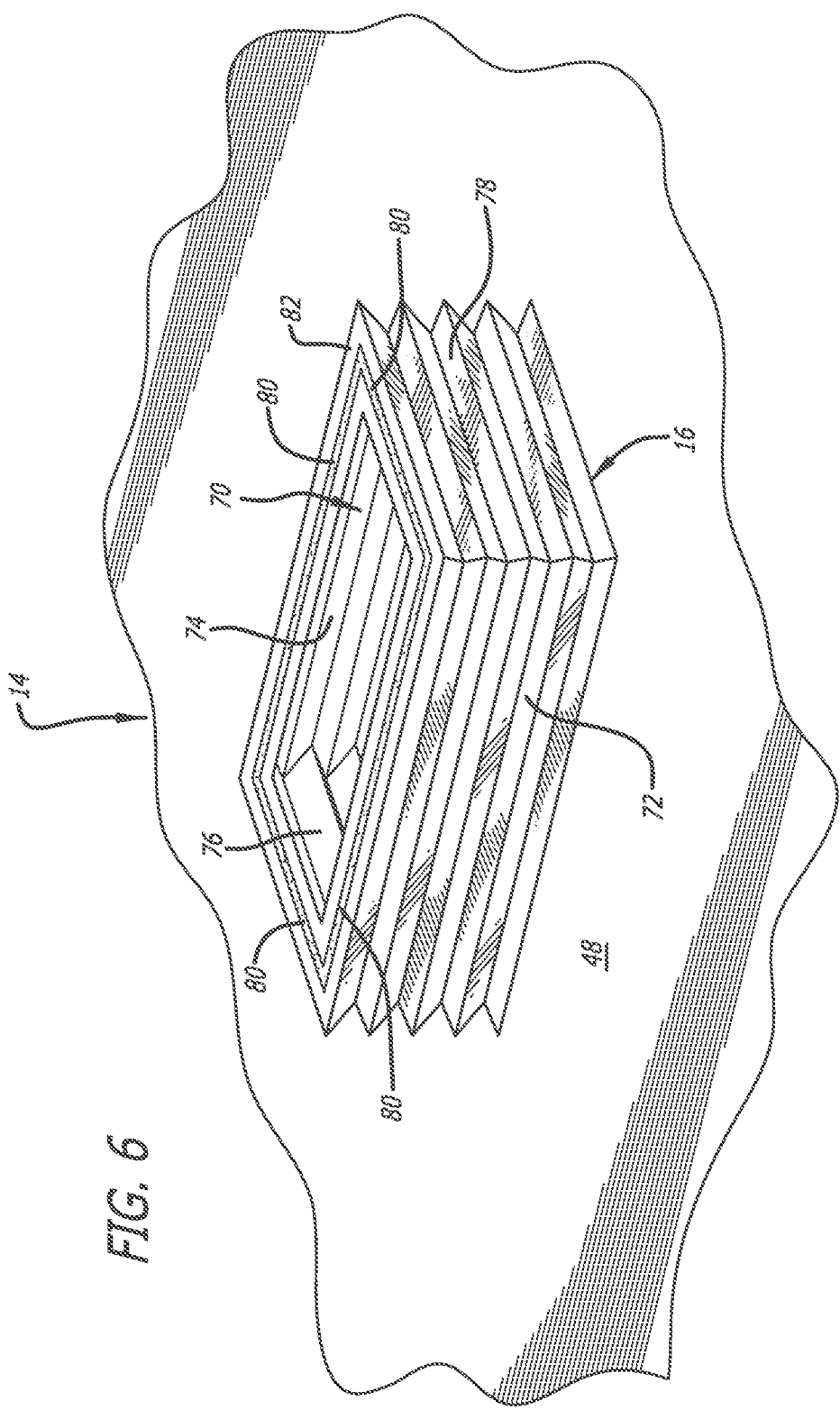
FIG. 6 is a perspective fragmentary view of the bottom of the over-draping and the connecting draping showing the connecting draping in an expanded position.

The connecting draping 16 can be made of sterile fabric materials affording expansion and contracting thereof. The connecting draping 16 can be made of an expandable and contractible elastic fabric. Furthermore, as depicted in FIGS. 4-6, the connecting draping 16 can be made of an expandable and contractible fabric bellows, or, in other words, a fabric having been folded in accordion folds. The fabric bellows can also include elastic properties. As depicted in FIGS. 5 and 6, the accordion folds allow the connecting draping 16 to expand and contract. For example, the connecting draping 16 can be formed from a first section 72, a second section 74, a third section 76, and a fourth section 78 each formed from a fabric folded in accordion folds that allow for expansion and contraction thereof.

The connecting draping 16 can be attached to the under-draping 12 and the over-draping 14 using adhesive materials formed thereon. For example, adhesive strips 80 can be provided on portions of the first section 72, the second section 74, the third section 76, and the forth section 78 to attach the connecting draping 16 to the under-draping 12 and the over-draping 14. To illustrate, as depicted in FIGS. 5 and 6, the adhesive strips 80 can be provided on a bottom surface 82 of the connecting draping 16, and these adhesive strips 80 can be used to attach the connecting draping 16 to the under-draping 12. Similarly, the adhesive strips 80 can be provided on a top surface (not shown) of the connecting draping 16, and these adhesive strips 80 can be used to attach the connecting draping 16 to the over-draping 14. Rather than using adhesive strips 80, the connecting draping 16 can be attached to the under-draping 12 and the over-draping 14 using, for example, liquid or solid adhesives, needle and thread, mechanical fasteners, or Velcro, or the like.

As discussed above, the apertures 30 and 60 can be one or more apertures, and can be sized, shaped, and oriented to correspond to the size and shape of the aperture 30. When more than one of the apertures 30 and 60 are used, additional connecting drapings 16 can be provided. That is, a first connecting draping 16 and its enclosed passageway 70 can be used with a first set of apertures 30 and 60 to provide a first sterile surgical corridor, and a second connecting draping 16 and its enclosed passageway 70 can be used with a second set of apertures 30 and 60 to provide a second sterile surgical corridor. As such, the first sterile surgical corridor can provide access to a first surgical site or sites, and the second sterile surgical corridor can provide access to a second surgical site or sites spaced, where the first and second surgical site or sites are spaced apart from one another on the patient P.

Additionally, to aid a surgeon during surgery, the over-draping 14 can include pockets 86 attached thereto. The pockets 86 can be used to store various extraneous surgical materials during surgery. Furthermore, as depicted in FIG. 12, a valley or gully 88 formed in the over-draping 14 during support thereof by the support stands 66 and 68 can also be used to hold extraneous surgical materials during surgery.

The under-draping 12, the over-draping 14, and the connecting draping 16 can be permanently or semi-permanently attached to one another at the above-discussed areas prior to placement relative to the patient P and the surgical table T. Furthermore, when permanently or semi-permanently attached to one another, the under-draping 12, the over-draping 14, and the connecting draping 16 can be packaged with one another. In doing so, the under-draping 12, the over-draping 14, and the connecting draping 16 can be folded to fit in a single package (not shown), and the folding of the under-draping 12, the over-draping 14, and the connecting 16 can serve in facilitating first the deployment of the under-draping 12 and then the deployment of the over-draping 14, or first the deployment of the over-draping 14 and then the deployment of the under-draping 12.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A surgical draping system for providing a sterile surgical corridor to at least two surgical sites on a patient during articulation of a surgical table positioned on an operating room floor and supporting the patient, the surgical draping system comprising:
    an under-draping adapted to be positioned on the patient, a portion of the under-draping adapted to be maintained in a substantially static position with respect to the patient, the portion of the under-draping including a first aperture therethrough, the first aperture being sized and adapted to afford access to the at least two surgical sites on the patient;
    an over-draping adapted for positioning over and separated from the under-draping and the patient, the over-draping adapted to be maintained in a substantially static position above the patient, the over-draping including a second aperture therethrough, the second aperture being sized and adapted to afford access to the at least two surgical sites on the patient;
    a connecting draping adapted for attachment between the under-draping and the over-draping, the connecting draping being expandable and contractible between a first position and a second position, the connecting draping including a first end, a second end, a third aperture formed at the first end, a fourth aperture formed at the second end, and an enclosed passageway therethrough from the third aperture at the first end to the fourth aperture at the second end, the first end being attached around the first aperture of the under-draping and the second end being attached around the second aperture of the over-draping to provide the sterile surgical corridor through the enclosed passageway between the first aperture of the under-draping and the second aperture of the over-draping to afford access to the at least two surgical sites;

wherein, when the under-draping is positioned over the patient, the over-draping is positioned over and separated from the under-draping and the patient and supported by a first support at and adjacent a first end of the patient, and by a second support at and adjacent a second end of the patient, and the connecting draping is attached to the under-draping and the over-draping to afford access to the at least two surgical sites through the sterile surgical corridor, portions of the connecting draping can expand and contract to maintain access to the at least two surgical sites through the sterile surgical corridor during articulation of the surgical table to position and reposition the patient supported on the surgical table.

2. The surgical draping system of claim 1, wherein the first aperture, the second aperture, and the enclosed passageway are configured to provide access to the at least two surgical sites at one of a right lateral side portion and a left lateral side portion of the patient, and one of an anterior portion and a posterior portion of the patient.

3. The surgical draping system of claim 1, wherein the over-draping includes a first pleating and a second pleating, the first and second pleatings providing slack in the over-draping.

4. The surgical draping system of claim 1, wherein the connecting draping is formed from an expandable and contractible elastic fabric.

5. The surgical draping system of claim 1, wherein the connecting draping is configured as a bellows to afford expansion and contraction of the connecting draping.

6. The surgical draping system of claim 1, wherein the connecting draping includes at least a first foldable portion, a second foldable portion, and a third foldable portion, the first, second, and third foldable portions affording expansion and contraction of the connecting draping.

7. A surgical draping system for providing a sterile surgical corridor to a patient during articulation of a surgical table positioned on an operating room floor and supporting the patient, the surgical draping system comprising:
  an under-draping adapted to be positioned on the patient with at least a portion of the under-draping adapted to be maintained in a substantially static position with respect to the patient, and the under-draping including a first aperture therethrough;
  an over-draping adapted to be positioned over and separated from the under-draping with at least a portion the over-draping adapted to be maintained in a substantially static position above the patient, and the over-draping including a second aperture therethrough;
  a connecting draping adapted for attachment between the under-draping and the over-draping, the connecting draping being expandable and contractible between a first position and a second position, the connecting draping including a first end, a second end, a third aperture formed at the first end, a fourth aperture formed at the second end, and an enclosed passageway therethrough from the third aperture at the first end to the fourth aperture at the second end, the first end being attached around the first aperture of the under-draping and the second end being attached around the second aperture of the over-draping to provide the sterile surgical corridor through the enclosed passageway between the first aperture of the under-draping and the second aperture of the over-draping.

8. The surgical draping system of claim 7, wherein the under-draping, the over-draping, and the connecting draping are adapted to afford access to at least two surgical sites on the patient.

9. The surgical draping system of claim 8, wherein the first aperture, the second aperture, and the enclosed passageway are sized and adapted to afford access to the at least two surgical sites on the patient.

10. The surgical draping system of claim 9, wherein the at least two surgical sites are at one of a right lateral side portion and a left lateral side portion of the patient, and one of an anterior portion and a posterior portion of the patient.

11. The surgical draping system of claim 7, wherein the over-draping includes a first pleating and a second pleating, the first and second pleatings providing slack in the over-draping.

12. The surgical draping system of claim 7, wherein the connecting draping is formed from an expandable and contractible elastic fabric.

13. The surgical draping system of claim 7, wherein the connecting draping is configured as a bellows to afford expansion and contraction of the connecting draping.

14. The surgical draping system of claim 7, wherein the connecting draping includes at least a first foldable portion, a second foldable portion, and a third foldable portion, the first, second, and third foldable portions affording expansion and contraction of the connecting draping.

15. A surgical draping system for providing a sterile surgical corridor to a patient during articulation of a surgical table positioned on an operating room floor and supporting the patient, the surgical draping system comprising:
  an under-draping adapted to be positioned on the patient with at least a portion of the under-draping adapted to be maintained in a substantially static position with respect to the patient, and the under-draping including a first aperture therethrough;
  an over-draping adapted to be positioned over and separated from the under-draping with at least a portion the over-draping adapted to be maintained in a substantially static position above the patient, and the over-draping including a second aperture therethrough;
  a connecting draping configured for attachment between the under-draping and the over-draping, the connecting draping being expandable and contractible between a first position and a second position, the connecting draping including a first end, a second end, a third aperture formed at the first end, a fourth aperture formed at the second end, and an enclosed passageway therethrough from the third aperture at the first end to the fourth aperture at the second end, the first end being attached around the first aperture of the under-draping and the second end being attached around the second aperture of the over-draping to provide the sterile surgical corridor through the enclosed passageway between the first aperture of the under-draping and the second aperture of the over-draping;
  wherein, the portions of the connecting draping can expand and contract to maintain access between the first aperture and the second aperture via the enclosed passageway during articulation of the patient using the surgical table.

16. The surgical draping system of claim 15, wherein the under-draping, the over-draping, and the connecting draping are adapted to afford access to at least two surgical sites on the patient.

17. The surgical draping system of claim 16, wherein the first aperture, the second aperture, and the enclosed passageway are sized and adapted to afford access to the at least two surgical sites on the patient.

18. The surgical draping system of claim 17, wherein the at least two surgical sites are at one of a right lateral side portion and a left lateral side portion of the patient, and one of an anterior portion and a posterior portion of the patient.

19. The surgical draping system of claim 15, wherein the over-draping includes a first pleating and a second pleating, the first and second pleatings providing slack in the over-draping.

* * * * *